(12) United States Patent
Schmitt et al.

(10) Patent No.: US 12,084,511 B2
(45) Date of Patent: Sep. 10, 2024

(54) PEPTIDE-BASED COMPOUNDS FOR USE IN THE PREVENTION, TREATMENT AND/OR DETECTION OF CANCER

(71) Applicant: Universitätsmedizin der Johannes Gutenberg-Universität Mainz, Mainz (DE)

(72) Inventors: Edgar Schmitt, Mainz (DE); Horst Kunz, Mainz (DE); Natascha Stergiou, Mainz (DE); Nikola Gaidzik, Heidelberg (DE)

(73) Assignee: Universitätsmedizin der Johannes Gutenberg-Universität Mainz, Mainz (DE)

( * ) Notice: Subject to any disclaimer, the term of this patent is extended or adjusted under 35 U.S.C. 154(b) by 1028 days.

(21) Appl. No.: 16/982,095

(22) PCT Filed: Mar. 18, 2019

(86) PCT No.: PCT/EP2019/056672
§ 371 (c)(1),
(2) Date: Sep. 18, 2020

(87) PCT Pub. No.: WO2019/179923
PCT Pub. Date: Sep. 26, 2019

(65) Prior Publication Data
US 2021/0130489 A1    May 6, 2021

(30) Foreign Application Priority Data
Mar. 21, 2018 (EP) ..................... 18163057

(51) Int. Cl.
*C07K 16/30* (2006.01)
*A61P 35/00* (2006.01)

(52) U.S. Cl.
CPC .......... *C07K 16/3092* (2013.01); *A61P 35/00* (2018.01); *C07K 2317/622* (2013.01)

(58) Field of Classification Search
CPC .......... C07K 16/3092; C07K 2317/622; C07K 14/4727; A61P 35/00; A61K 39/0011
See application file for complete search history.

(56) References Cited

U.S. PATENT DOCUMENTS

| | | | |
|---|---|---|---|
| 9,546,201 B2 | 1/2017 | Kufe et al. | |
| 2016/0176975 A1 | 6/2016 | Clausen et al. | |

FOREIGN PATENT DOCUMENTS

| | | | |
|---|---|---|---|
| CN | 103483453 | 1/2014 | |
| CN | 107184602 | 9/2017 | |
| WO | WO2013103658 | 7/2013 | |
| WO | WO2013185552 | 12/2013 | |
| WO | WO-2013185552 A1 * | 12/2013 | ........... A61K 38/177 |

OTHER PUBLICATIONS

Haidar JN et al. A universal combinatorial design of antibody framework to graft distinct CDR sequences: A bioinformatics approach. Proteins: Structure, function, and bioinformatics 2012 80(3) 896-912 (Year: 2012).*
Brown M et al., Tolerance of single, but not multiple, amino acid replacements in antibody VH CDR 2: a means of minimizing B cell wastage from somatic hypermutation? J. Immunol., 1996 156(9):3285-91 (Year: 1996).*
Almagro JC et. al., Progress and Challenges in the Design and Clinical Development of Antibodies for Cancer Therapy Front. Immunol. 2018; 8:1751 (Year: 2018).*
Wagner HJ et al. A Two-Step Approach for the Design and Generation of Nanobodies. Int. J. Mol. Sci. 2018, 19, 3444 1-16 (Year: 2018).*
Singh R et al. MUC1 A Target Molecule for Cancer Therapy. Cancer Biology & Therapy 2007 6:4, 481-486 (Year: 2007).*
English translation of WO2013185552 (Qian Q et al.) (Year: 2024).*
Brockahusen, I. et al, "Mechanisms underlying aberrant glycosylation of MUC1 mucin in breast cancer cells", Eur. J. Biochem., vol. 233, pp. 607-617, (1995).
Arklie, J. et al, "Differentiation antigens expressed by epithelial cells in the lactating breast are also detectable in breast cancers", Int. J. Cancer, vol. 28, pp. 23-29, https://doi.org/10.1002/ijc.2910280105, (1981) Abstract.
Hanisch, F. et al, "Structures of acidic O-linked polylactosaminoglycans on human skim milk mucins", Glycoconjugate J., vol. 7, pp. 525-543, (1990).
Domenech, N. et al, "Identification of an HLA-A11-restricted epitope from the tandem repeat domain of the epithelial tumor antigen mucin", J. Immunol., vol. 155, pp. 4766-4774, (1995) Abstract.
Sames, D. et al, "Convergent total synthesis of a tumour-associated mucin motif", Nature, vol. 389, pp. 587-591, (1997) Abstract.
Liebe, B. et al, "Solid-phase synthesis of a tumor-associated Sialyl-Tn antigen glycopeptide with a partial sequence of the "Tandem Repeat" of the MUC-1 Mucin", Chem. Int. Ed. Engl., vol. 36(6), pp. 618-621, https://doi.org/10.1002/anie.199706181, (1997) Abstract.
Anonymous, "Nomenclature and symbolism for amino acids and peptides", Pure & Applied Chem., vol. 56(5), pp. 595-624, (1984).

(Continued)

*Primary Examiner* — Julie Wu
*Assistant Examiner* — John J Skoko, III
(74) *Attorney, Agent, or Firm* — McHale & Slavin, P.A.

(57) ABSTRACT

The present invention relates to a compound comprising a first polypeptide sequence comprising at least three different amino acid sequences selected from the group consisting of GFTFSDYW (SEQ ID NO: 1), IRLKSNNYAA (SEQ ID NO: 2) and TFGNSFAY (SEQ ID NO: 3), a second polypeptide sequence comprising at least three different amino acid sequences selected from the group consisting of TGAVTTNNY (SEQ ID NO: 4), GTN (SEQ ID NO: 5) and ALWYSNHWV (SEQ ID NO: 6), or a variant of any one of said amino acid sequences of SEQ ID NO: 1 to SEQ ID NO: 6 having a different amino acid at one position, wherein said compound or variant is capable of binding to tumour-associated Mucin-1 (TA-MUC1).

11 Claims, 5 Drawing Sheets
Specification includes a Sequence Listing.

(56) References Cited

OTHER PUBLICATIONS

Gendler, S. et al, "Molecular cloning and expression of human tumor-associated polymorphic epithelial mucin", J. Bio. Chem., vol. 265, pp. 15286-15293, (1990).

Nath, S., "MUC1: a multifaceted oncoprotein with a key role in cancer progression", Trends in Molecular Medicine, vol. 20(6), pp. 332-342, https://doi.org/10.1016/J.MOLMED.2014.02.007, (Jun. 2014).

* cited by examiner

SEQUENCE LISTING

```
<160> NUMBER OF SEQ ID NOS: 19

<210> SEQ ID NO 1
<211> LENGTH: 8
<212> TYPE: PRT
<213> ORGANISM: Mus musculus

<400> SEQUENCE: 1

Gly Phe Thr Phe Ser Asp Tyr Trp
1               5

<210> SEQ ID NO 2
<211> LENGTH: 10
<212> TYPE: PRT
<213> ORGANISM: Mus musculus

<400> SEQUENCE: 2

Ile Arg Leu Lys Ser Asn Asn Tyr Ala Ala
1               5                   10

<210> SEQ ID NO 3
<211> LENGTH: 8
<212> TYPE: PRT
<213> ORGANISM: Mus musculus

<400> SEQUENCE: 3

Thr Phe Gly Asn Ser Phe Ala Tyr
1               5

<210> SEQ ID NO 4
<211> LENGTH: 9
<212> TYPE: PRT
<213> ORGANISM: Mus musculus

<400> SEQUENCE: 4

Thr Gly Ala Val Thr Thr Asn Asn Tyr
1               5

<210> SEQ ID NO 5
<211> LENGTH: 3
<212> TYPE: PRT
<213> ORGANISM: Mus musculus

<400> SEQUENCE: 5

Gly Thr Asn
1

<210> SEQ ID NO 6
```

```
<211> LENGTH: 9
<212> TYPE: PRT
<213> ORGANISM: Mus musculus

<400> SEQUENCE: 6

Ala Leu Trp Tyr Ser Asn His Trp Val
1               5

<210> SEQ ID NO 7
<211> LENGTH: 117
<212> TYPE: PRT
<213> ORGANISM: Mus musculus

<400> SEQUENCE: 7

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Asp Ile Arg Leu Lys Ser Asn Asn Tyr Ala Ala His Tyr Ala Glu
        50                  55                  60

Ser Val Lys Gly Arg Phe Thr Val Ser Arg Asp Asp Ser Lys Ser Ser
65                  70                  75                  80

Val Tyr Leu Gln Met Asn Asn Leu Arg Thr Glu Asp Thr Gly Phe Tyr
                85                  90                  95

Tyr Cys Thr Phe Gly Asn Ser Phe Ala Tyr Trp Gly Gln Gly Thr Leu
            100                 105                 110

Val Thr Val Ser Ala
        115

<210> SEQ ID NO 8
<211> LENGTH: 109
<212> TYPE: PRT
<213> ORGANISM: Mus musculus

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Asn
                20                  25                  30

Asn Tyr Ala Asn Trp Val Gln Glu Lys Pro Asp His Leu Phe Thr Gly
            35                  40                  45

Leu Ile Gly Gly Thr Asn Asn Arg Gly Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 9
<211> LENGTH: 246
<212> TYPE: PRT
<213> ORGANISM: Mus musculus

<400> SEQUENCE: 9

Glu Val Lys Leu Glu Glu Ser Gly Gly Gly Leu Val Gln Pro Gly Gly
```

```
            1               5                   10                  15
        Ser Met Lys Leu Ser Cys Val Ala Ser Gly Phe Thr Phe Ser Asp Tyr
                        20                  25                  30

Trp Met Asn Trp Val Arg Gln Ser Pro Glu Lys Gly Leu Glu Trp Val
                        35                  40                  45

Ala Asp Ile Arg Leu Lys Ser Asn Asn Tyr Ala His Tyr Ala Glu
                        50                  55                  60

Ser Val Lys Gly Arg Phe Thr Val Ser Arg Asp Asp Ser Lys Ser Ser
        65                      70                  75                  80

Val Tyr Leu Gln Met Asn Asn Leu Arg Thr Glu Asp Thr Gly Phe Tyr
                        85                  90                  95

Tyr Cys Thr Phe Gly Asn Ser Phe Ala Tyr Trp Gly Gln Gly Thr Leu
                        100                 105                 110

Val Thr Val Ser Ala Gly Gly Gly Gly Ser Gly Gly Gly Ser Gly
                        115                 120                 125

Gly Gly Ser Gly Gly Gly Ser Gln Ala Val Val Thr Gln Glu
                        130                 135                 140

Ser Ala Leu Thr Thr Ser Pro Gly Glu Thr Val Thr Leu Thr Cys Arg
        145                     150                 155                 160

Ser Ser Thr Gly Ala Val Thr Thr Asn Asn Tyr Ala Asn Trp Val Gln
                        165                 170                 175

Glu Lys Pro Asp His Leu Phe Thr Gly Leu Ile Gly Thr Asn Asn
                        180                 185                 190

Arg Gly Pro Gly Val Pro Ala Arg Phe Ser Gly Ser Leu Ile Gly Asp
                        195                 200                 205

Lys Ala Ala Leu Thr Ile Thr Gly Ala Gln Thr Glu Asp Glu Ala Ile
                        210                 215                 220

Tyr Phe Cys Ala Leu Trp Tyr Ser Asn His Trp Val Phe Gly Gly Gly
        225                     230                 235                 240

Thr Lys Leu Thr Val Leu
                        245

<210> SEQ ID NO 10
<211> LENGTH: 20
<212> TYPE: PRT
<213> ORGANISM: Homo sapiens

<400> SEQUENCE: 10

Pro Ala His Gly Val Thr Ser Ala Pro Asp Thr Arg Pro Ala Pro Gly
1               5                   10                  15

Ser Thr Ala Pro
            20

<210> SEQ ID NO 11
<211> LENGTH: 17
<212> TYPE: PRT
<213> ORGANISM: Artificial Sequence
<220> FEATURE:
<223> OTHER INFORMATION: artificial linker sequence

<400> SEQUENCE: 11

Met Asn Trp Val Arg Gln Ser Pro Glu Lys Gly Leu Glu Trp Val Ala
1               5                   10                  15

Asp

<210> SEQ ID NO 12
<211> LENGTH: 38
```

```
<212> TYPE: PRT
<213> ORGANISM: Artificial Sequence
<220> FEATURE:
<223> OTHER INFORMATION: artificial linker sequence

<400> SEQUENCE: 12

His Tyr Ala Glu Ser Val Lys Gly Arg Phe Thr Val Ser Arg Asp Asp
1               5                   10                  15

Ser Lys Ser Ser Val Tyr Leu Gln Met Asn Asn Leu Arg Thr Glu Asp
            20                  25                  30

Thr Gly Phe Tyr Tyr Cys
            35

<210> SEQ ID NO 13
<211> LENGTH: 17
<212> TYPE: PRT
<213> ORGANISM: Artificial Sequence
<220> FEATURE:
<223> OTHER INFORMATION: artificial linker sequence

<400> SEQUENCE: 13

Ala Asn Trp Val Gln Glu Lys Pro Asp His Leu Phe Thr Gly Leu Ile
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: artificial linker sequence

<400> SEQUENCE: 14

Ala Asn Trp Val Gln Glu Lys Pro Asp His Leu Phe Thr Gly Leu Ile
1               5                   10                  15

Gly

<210> SEQ ID NO 15
<211> LENGTH: 19
<212> TYPE: DNA
<213> ORGANISM: Homo sapiens

<400> SEQUENCE: 15
gtgcccccta gcagtaccg                                              19

<210> SEQ ID NO 16
<211> LENGTH: 20
<212> TYPE: DNA
<213> ORGANISM: Homo sapiens

<400> SEQUENCE: 16
gacgtgcccc tacaagttgg                                             20

<210> SEQ ID NO 17
<211> LENGTH: 22
<212> TYPE: DNA
<213> ORGANISM: Homo sapiens

<400> SEQUENCE: 17
tggatgctcc aggccataag ga                                          22

<210> SEQ ID NO 18
<211> LENGTH: 22
```

```
<212> TYPE: DNA
<213> ORGANISM: Homo sapiens

<400> SEQUENCE: 18
tgctctcgtg tttgtcctcc ag                                          22

<210> SEQ ID NO 19
<211> LENGTH: 36
<212> TYPE: PRT
<213> ORGANISM: Mus musculus

<400> SEQUENCE: 19

Asn Arg Gly Pro Gly Val Pro Ala Arg Phe Ser Gly Ser Leu Ile Gly
1               5                   10                  15

Asp Lys Ala Ala Leu Thr Ile Thr Gly Ala Gln Thr Glu Asp Glu Ala
            20                  25                  30

Ile Tyr Phe Cys
        35
```

PEPTIDE-BASED COMPOUNDS FOR USE IN THE PREVENTION, TREATMENT AND/OR DETECTION OF CANCER

CROSS REFERENCE TO RELATED APPLICATIONS

This is a national stage filing in accordance with 35 U.S.C. § 371 of PCT/EP2019/056672, filed Mar. 18, 2019, which claims the benefit of the priority of European Patent Application No. 18163057.5, filed Mar. 21, 2018, the contents of each are incorporated herein by reference.

TECHNICAL FIELD

The present invention relates to novel compounds with the ability to bind to mammalian tumour-associated Mucin-1 (TA-MUC1) which can be found in MUC1-expressing tumour tissues. The compounds of the invention are suitable for the treatment, prevention or detection of cancer such as pancreatic cancer, prostate cancer, breast cancer, B cell leukemia, multiple myeloma, colon cancer and ovarian cancer. As such, the compounds of the invention allow the differentiation between TA-MUC1 as found in epithelial tumour cells and MUC-1 as found in healthy epithelial cells. The inventive compounds are thus suitable as tumour targeting agents for use in therapeutic and diagnostic applications.

PRIOR ART

MUC1 is a heavily glycosylated protein expressed on many epithelial tissues and can be found, for example, in breast, colon, prostate and pancreas tissues as well as in the ovaries (M. A. Hollingsworth, B. J. Swanson, Nat. Rev. Cancer 2004, 4, 45-60). The extracellular part of MUC1 contains a domain that consists of 20 to 100 repetitive copies of the sequence PAHGVTSAPDTRPAPGSTAP, including five O-glycosylation sites at serine or threonine. Normally, MUC1 carries long glycans, which force the protein to adopt an extended conformation. Due to the dense glycosylation, the peptide backbone is inaccessible to the immune system. The glycans of TA-MUC1 are much shorter and often prematurely sialylated (J. Arklie, J. Taylor-Papadimitrious et al., Int. J. Cancer 1981, 28, 23-29; I. Brockhausen et al., Eur. J. Biochem. 1995, 233, 607-617; F.-G. Hanisch et al., Glycoconjugate J. 1990, 7, 525-543; N. Doménech et al., J. Immunol. 1995, 155, 4766-4774).

The application of such glycoproteins in the course of an immunotherapy could cause un-wanted severe autoimmune reactions against normal MUC1. Because pure TA-MUC1-glycopeptide antigens cannot be isolated from tumour cells, they must be obtained by chemical total synthesis (D. Sames et al., Nature 1997, 389, 587-559; B. Liebe, H. Kunz, Angew. Chem. Int. Ed. Engl. 1997, 36, 618-621; Angew. Chem. 1997, 109, 629-631).

O-glycans are incompletely processed in cancer cells resulting in the expression of the pancarcinoma carbohydrate antigens Tn (GalNAcα1-O-Ser/Thr), STn (NeuAcα2-6GalNAcα1-O-Ser/Thr), and T (Galβ1-3GalNAcα1-O-Ser/Thr). MUC1 expressed by breast carcinoma cells carries the short cancer-associated Tn, STn, and T antigens as well as the mono- and disialyl core 1 structure (ST, NeuAcα2-3Galβ1-3[NeuAcα2-6]+/−GalNAcα1-O-Ser/Thr) found widely in normal cells. In contrast, MUC1 expressed in normal breast epithelial cells generally carry branched core 2 O-glycans (Galβ1-3 [GlcNAcβ1-6]GalNAcα1-O-Ser/Thr) with lactosamine extensions.

The cell membrane-bound MUC1 has long been considered a prime target for immunotherapeutic intervention. However, stimulation of an effective cellular or humoral immune response to cancer-associated forms of MUC1 in patients or transgenic animals expressing the human MUC1 gene (using defined immunogens as opposed to cell based therapies) have not been achieved. Strategies for active specific immunotherapy based on peptide/protein immunogens have so far been limited to unglycosylated MUC1 tandem repeat peptides of different lengths, conjugated to different carriers, or administered with an adjuvant. These strategies have generally failed to produce effective immune responses to MUC1 expressed by cancer cells in hosts where the mucin is expressed as a self-antigen.

The N-terminal subunit of MUC1 that contains the variable numbers of tandem repeats with a high proportion of serines and threonines that are modified by O-glycosylation extends beyond the glycocalyx of the cell and is tethered to the cell surface through noncovalent binding to the transmembrane C-terminal subunit of MUC1 (Merlo, 1989). The C-terminus consists of a 58-amino acid extracellular domain, a 28-amino acid transmembrane domain and a 72-amino acid cytoplasmic domain that interacts with diverse signalling molecules (Kufe, 2008).

In the past, a large number of monoclonal antibodies (mAbs) have been produced to purify MUC1 and synthetic peptides and glycopeptides derived from MUC1. The epitopes of these mAbs have traditionally been defined by scanning overlapping short peptides, and most of the mAbs define epitopes in the heavily O-glycosylated mucin tandem repeat domain. One large group of mAbs has been raised against human milk fat globule (HMFG) including HMFG1, 115D8, and SM3, most of which react with an epitope in the PDTR region of the MUC1 tandem repeat considered to be the immunodominant peptide epitope. Most MUC1 antibodies react with the peptide backbone but often the binding is modulated by the presence of glycans. On tumour cells, the peptide backbone of MUC1 is accessible to the immune system but seemed to be hampered by the residual aberrant glycosylation (I. Brockhausen et al., Eur. J. Biochem. 1995, 233, 607-617; S. J. Gendler et al., J. Biol. Chem. 1990, 265, 15286-15293).

TA-MUC1 differs from the MUC1 expressed in normal cells with regard to its biochemical features, cellular distribution, and function (Nath et al., Trends in Molecular Medicine, Volume 20, Issue 6, p 332-342, June 2014). In cancer cells, MUC1 participates in intracellular signal transduction pathways and regulates the expression of its target genes at both the transcriptional and post-transcriptional levels.

However, to utilize this structural difference for immunotherapy and diagnostic purposes, the immune system must be activated specifically against these TA-MUC1 structures. This can only be achieved with complex synthetic glycopeptides which mimic antigens that represent a unique component selectively of tumour-associated MUC1. As the transferase activities of tumour cells are inherently very variable both normal and tumour-associated glycans can be found on a single MUC1 molecule allowing the generation of novel compounds suitable for specifically targeting TA-MUC1 as found on epithelial tumour cells.

US 2016/0176975 A1 describes a method for inducing a cancer-specific immune response against TA-MUC1 using an immunogenic glycopeptide comprising a GSTA motif, which is O-glycosylated at the S/T residue (ST$_N$/T$_N$ antigen). In particular, monoclonal antibodies such as mAb 5E5, 5E10, 1B9, 2D9 are compared to known mAbs previously reported such as SM3, BW835.

U.S. Pat. No. 9,546,201 B2 describes peptides from a particular region of the MUC1 cytoplasmic domain that have shown to inhibit MUC1 oligomerization and nuclear translocation, and methods for preventing tumour cell growth by inducing tumour cell apoptosis and necrosis of tumour tissue in vivo. The oligomer-inhibiting peptides comprise no more than twenty consecutive residues of the amino acid sequence CQCRRKN and a cell delivery domain like poly-D-R covering the amino-terminal cysteine of said peptide. The peptide can be applied to any cell that expresses MUC1, and more particularly, that overexpresses MUC1.

WO 2013/185552 A1 discloses a chimeric antigen receptor for treating malignant tumour and virus infectious diseases. CN 107 184 602 A and CN 103 483 453 A also disclose a chimeric antigen receptor for use in treating tumours. WO 2013/103658 A1 discloses peptides comprising epitopes from the human tumour-associated (TA) antigen Mucin1 (MUC1) for use in the prevention or treatment of cancer via vaccination.

It is still desirable however to obtain a compound that is capable to specifically differentiate between normal MUC1 as found in healthy epithelial cells and TA-MUC1 as found in tumour tissue to obtain a high rate of tumour-selective recognition in order to be suitable/serve as an active agent for clinical applications in the treatment, prevention and/or diagnosis of tumour entities that are expressing TA-MUC1.

SUMMARY OF THE INVENTION

It is therefore an object of the invention to provide alternative compounds that allow for differentiation between TA-MUC1 and normal MUC1 as found in healthy epithelial cells, and that are suitable for the treatment, prevention and diagnosis of cancer that comprises tumour cells that specifically express tumour-associated MUC1.

This object is solved by peptide-based compounds as claimed in claim 1. Preferred embodiments of the invention are part of the sub-claims.

The inventive compounds were obtained by immunisation with a specific MUC1-derived glycopeptide mimicking the structure of TA-MUC1 on epithelial tumour cells and comprise one or more polypeptide sequences containing specific binding sites required for binding to mammalian TA-MUC1. Surprisingly, the binding sites as identified in the invention are specific for TA-MUC1 but not for normal MUC1 as found on healthy epithelial tissue. Thus, the compounds of the invention are suitable for the differentiation between tumour cells expressing TA-MUC1 and healthy cells expressing normal MUC1. The binding sites of the compounds of the invention have been identified by using an immunogenic vaccine that resulted in the generation of TA-MUC1-specific murine mAb. The amino acid sequences of the binding sites and the binding regions of one mAb have been identified and are defined herein as SEQ ID NO: 1 to SEQ ID NO: 6.

The polypeptide-based compounds containing the binding sites that are specific for binding to mammalian TA-MUC1, preferably human TA-MUC1 (hu-TA-MUC1) comprise:
- a first polypeptide sequence comprising at least three different amino acid sequences selected from the group consisting of GFTFSDYW (SEQ ID NO: 1), IRLKSNNYAA (SEQ ID NO: 2) and TFGNSFAY (SEQ ID NO: 3),
- a second polypeptide sequence comprising at least three different amino acid sequences selected from the group consisting of TGAVTTNNY (SEQ ID NO: 4), GTN (SEQ ID NO: 5) and ALWYSNHWV (SEQ ID NO: 6), or a variant of any one of said amino acid sequences of SEQ ID NO: 1 to SEQ ID NO: 6 having a different amino acid at one or more positions, wherein said compound or variant is capable of binding TA-MUC1.

Accordingly, the amino acid sequences of SEQ ID NO: 1 to SEQ ID NO: 3 of the first polypeptide sequence bearing the binding sites for binding to TA-MUC1 can be arranged in the form of:

GFTFSDYW- (SEQ ID NO: 1)

IRLKSNNYAA- (SEQ ID NO: 2)

TFGNSFAY, (SEQ ID NO: 3)

GFTFSDYW- (SEQ ID NO: 1)

TFGNSFAY- (SEQ ID NO: 3)

IRLKSNNYAA, (SEQ ID NO: 2)

IRLKSNNYAA- (SEQ ID NO: 2)

TFGNSFAY- (SEQ ID NO: 3)

GFTFSDYW, (SEQ ID NO: 1)

IRLKSNNYAA- (SEQ ID NO: 2)

GFTFSDYW- (SEQ ID NO: 1)

TFGNSFAY, (SEQ ID NO: 3)

TFGNSFAY- (SEQ ID NO: 3)

GFTFSDYW- (SEQ ID NO: 1)

IRLKSNNYAA, (SEQ ID NO: 2)

TFGNSFAY- (SEQ ID NO: 3)

IRLKSNNYAA- (SEQ ID NO: 2)

GFTFSDYW. (SEQ ID NO: 1)

Similarly, amino acid sequences of SEQ ID NO: 4 to SEQ ID NO: 6 of the second polypeptide sequence bearing the further binding sites required for binding to mammalian TA-MUC1, preferably hu-TA-MUC1, can be arranged in the form of:

TGAVTTNNY- (SEQ ID NO: 4)

GTN- (SEQ ID NO: 5)

ALWYSNHWV, (SEQ ID NO: 6)

TGAVTTNNY- (SEQ ID NO: 4)

ALWYSNHWV- (SEQ ID NO: 6)

GTN, (SEQ ID NO: 5)

GTN- (SEQ ID NO: 5)

TGAVTTNNY- (SEQ ID NO: 4)

ALWYSNHWV, (SEQ ID NO: 6)

GTN- (SEQ ID NO: 5)

ALWYSNHWV- (SEQ ID NO: 6)

TGAVTTNNY, (SEQ ID NO: 4)

ALWYSNHWV- (SEQ ID NO: 6)

TGAVTTNNY- (SEQ ID NO: 4)

GTN, (SEQ ID NO: 5)

ALWYSNHWV- (SEQ ID NO: 6)

GTN- (SEQ ID NO: 5)

TGAVTTNNY. (SEQ ID NO: 4)

The invention also comprises variants of any one of said amino sequences as defined under SEQ ID NO: 1 to SEQ ID NO: 6 comprising one or more amino acid substitutions at one or more positions within the amino acid sequence. However, the invention only covers variants that are able to bind to mammalian TA-MUC1, preferably hu-TA-MUC1, thus retaining the binding specificity of the inventive compound. A variant can also comprise amino acid sequences homologous to SEQ ID NO: 1 to SEQ ID NO: 6 found in the corresponding binding regions in different mammalian species such as human homologous sequences.

Having a different amino acid at one or more positions in any of the amino acid sequences of SEQ ID NO: 1 to SEQ ID NO: 6 means that more one, two, three or more amino acids can differ from the sequence outlined in SEQ ID NO: 1 to SEQ ID NO: 2, either by substitution, addition, deletion or modification. Preferably, in such a variant 1, 2, 3 or 4 amino acids in a given amino acid sequence are substituted by one ore more alternative amino acid(s). In a preferred embodiment not more than 3, preferably not more than 2 amino acids are replaced by another amino acid.

A variant according to the present invention may comprise an amino acid sequence which has at least 70% positive amino acid matches, more preferably at least 90% positive amino acid matches, for example 91% to 99% positive amino acid matches with a selected amino acid sequence of any one of SEQ ID NO: 1 to SEQ ID NO: 6. A positive amino acid match is defined as the presence at the same position in two compared sequences of amino acid residues which has similar physical, biological and/or chemical properties. Preferred positive amino acid matches that could be used for substitutions are K to R, E to D, L to M, Q to E, I to V, I to L, A to S, Y to W, K to Q, S to T, N to S and Q to R. It is required that a peptide or variant of the present invention has the capability of specifically binding to mammalian TA-MUC1 in tumour cells but not to normal MUC1 as found in normal cells.

A compound or variant according to the present invention may also comprise other chemical moieties such as phosphoryl, sulphur, acetyl, or glycosyl moieties. As such, a given amino acid sequence may be modified, for example, by addition, deletion, substitution or chemical modification of one or more of the amino acid residues. For such modifications, both L-amino acids and D-amino acids may be used. Possible chemical modifications may comprise derivatives such as sugars or esters, for example methyl or acetyl esters, or polyethylene glycol modifications. Furthermore, an amine group of the peptide may be converted to an amide, which comprises a fatty acid. A peptide or variant of the invention can also be modified by biotin at it C-terminus or by a His-Tag at its N-terminus.

According to the present invention, variants of the amino acid sequences may comprise one or more conservative amino acid substitutions, which are independent of one another, wherein
(i) at least one glycine (Gly) of said variant is substituted with an amino acid selected from the group of amino acids consisting of Ala, Val, Leu, and Ile,
(ii) at least one alanine (Ala) of said variant is substituted with an amino acid selected from the group of amino acids consisting of Gly, Val, Leu,
(iii) at least one valine (Val) of said variant is substituted with an amino acid selected from the group of amino acids consisting of Gly, Ala, Leu, and Ile,
(iv) at least one leucine (Leu) of said variant is substituted with an amino acid selected from the group of amino acids consisting of Gly, Ala, Val, and Ile,
(v) at least one isoleucine (Ile) of said variant is substituted with an amino acid selected from the group of amino acids consisting of Gly, Ala, Val and Leu,
(vi) at least one aspartic acids (Asp) of said variant is substituted with an amino acid selected from the group of amino acids consisting of Glu, Asn, and Gln,
(vii) at least one asparagine (Asn) of said variant is substituted with an amino acid selected from the group of amino acids consisting of Asp, Glu, and Gln,
(viii) at least one glutamine (Gln) of said variant is substituted with an amino acid selected from the group of amino acids consisting of Asp, Glu, and Asn,
(ix) at least one phenylalanine (Phe) of said variant is substituted with an amino acid selected from the group of amino acids consisting of Tyr, Trp, His, Pro, preferably selected from the group of amino acids consisting of Tyr and Trp,
(x) at least one tyrosine (Tyr) of said variant is substituted with an amino acid selected from the group of amino acids consisting of Phe, Trp, His, Pro, preferably an amino acid selected from the group of amino acids consisting of Phe and Trp, (xi) at least one arginine (Arg) of said variant is substituted with an amino acid selected from the group of amino acids consisting of Lys and His, (xii) at least one lysine (Lys) of said variant is substituted with an amino acid selected from the group of amino acids consisting of Arg and His (xiii) at least one proline (Pro) of said variant is substituted with an amino acid selected from the group of amino acids consisting of Phe, Tyr, Trp, and His, (xiv) at least one cysteine (Cys) of said variant is substituted with an amino acid selected from the group of amino acids consisting of Asp, Glu, Lys, Arg, His, Asn, Gln, Ser, Thr, and Tyr.

It thus follows from the above that the same variant of a compound of the invention may comprise more than one conservative or homologous amino acid substitution from more than one group of conservative amino acids as defined herein above.

Conservative amino acid substitutions may be introduced into any position of a polypeptide sequence of the present invention. It may however also be desirable to introduce non-conservative substitutions, particularly, but not limited to, a non-conservative substitution at one or more positions. Substitutions of amino acids may be made based upon their hydrophobicity and hydrophilicity values and the relative similarity of the amino acid side-chain substituents such as size and charge.

The groups of conservative amino acids are preferably the following, depending on their known chemical properties:
(i) A, G; (ii) Q, N, S, T; (iii) E, D; (iv) Q, N, S, T; (v) H, K, R; (vi) L, P, I, V, M, F, Y, W In the context of the present invention, the standard one-letter code for amino acid residues as well as the standard three-letter code are applied. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified, it is to be understood that the amino acid in question has the natural L form, cf. Pure & Appl. Chem. Vol. 56(5) pp 595-624 (1984), or the D form, so that the peptides formed may be constituted of amino acids of L form, D form, or a sequence of mixed L forms and D forms.

The C-terminal amino acid of a peptide usually exists as a free carboxylic acid, which may also be specified as "—OH". However, the C-terminal amino acid of a peptide for use according to the present invention may also be an amidated derivative, which is specified as "—NH-2". Where nothing else is stated, the N-terminal amino acid of a polypeptide comprises a free amino-group, sometimes also specified as "H–". A peptide, fragment or variant thereof according to the present invention can also comprise one or more unnatural or modified natural amino acids.

In a preferred embodiment of the invention, the different amino acid sequences containing the binding sites for binding mammalian TA-MUC1, preferably hu-TA-MUC1, are arranged as follows in the inventive compound:

a first polypeptide sequence comprising the structure A1-x-A2-y-A3, wherein
A1 comprises an amino acid sequence as set forth in SEQ ID NO: 1,
A2 comprises an amino acid sequence as set forth in SEQ ID NO: 2,
A3 comprises an amino acid sequence as set forth in SEQ ID NO: 3,
x, y are >=0 linking amino acids;
a second polypeptide sequence having the structure A4-x-A5-y-A6, wherein
A4 comprises an amino acid sequence as set forth in SEQ ID NO: 4,
A5 comprises an amino acid sequence as set forth in SEQ ID NO: 5,
A6 comprises an amino acid sequence as set forth in SEQ ID NO: 6,
x, y are >=0 linking amino acids,
or a variant of any one of said amino acid sequences of SEQ ID NO: 1 to SEQ ID NO: 6 having a different amino acid at one or more positions. According to the invention, said compound or variant is capable of binding to TA-MUC1.

The linking amino acids x or y may be random amino acids of various length. A typical length of x or y is between 15 and 70 amino acids, whereas a number of not more than 75 amino acids is preferred. If x or y=0, this means that no linking amino acid is present to connect the TA-MUC1 binding sites as defined in the amino acid sequences SEQ ID NO: 1 to SEQ ID NO: 6.

In a preferred embodiment of the first polypeptide sequence, x designates the amino acid sequence MNWVRQSPEKGLEWVAD (SEQ ID NO: 11), or a variant of that amino acid sequence having a different amino acid at one or more positions. In a preferred embodiment of the first polypeptide sequence, y designates the amino acid sequence HYAESVKGRFTVSRD DSKSSVYLQMNNLRTEDTGFYYC (SEQ ID NO: 12), or variants of said amino acid sequence having a different amino acid at one or more positions.

In a preferred embodiment of the second polypeptide sequence x designates the amino acid sequence ANWVQEKPDHLFTGLIG (SEQ ID NO: 13), or a variant of said amino acid sequence having a different amino acid at one or more positions. In a preferred embodiment of the second polypeptide sequence y designates the amino acid sequence NRGPGVPARFSGSLIGDKAA LTITGAQT-EDEAIYFC (SEQ ID NO: 19), or a variant of said amino acid sequence having a different amino acid at one or more positions.

All variants of the present invention, including homologous binding sequences found in other species shall have the biological activity of recognizing and binding mammalian TA-MUC1, preferably hu-TA-MUC1.

In a preferred embodiment, the first polypeptide sequence and the at least one second polypeptide sequence are covalently coupled by an additional linker.

Preferably, the linker comprises one or more amino acids between 1 and 25 amino acids, selected from the group consisting of S and G. As such, the linker is enriched in the amino acids S and G, for example in the form of SGGGGS. However, the linker may also contain one or more different amino acids within the sequence or at its ends.

Preferably the compound of the invention is a protein, antibody, single chain fragment variable (scFv) or a hybrid fusion protein. A hybrid fusion protein can be the compound of the invention coupled to another protein such as an enzyme, antibody (fragment), or cytokine.

In a preferred embodiment, the compound of the invention can be labelled with $^{89}$Zr or $^{117}$Lu. $^{89}$Zr is suitable for analytical imaging for detecting cancer tissue that expresses TA-MUC1. $^{117}$Lu is suitable as beta radiator for tumour therapy as this compound is able to destroy tumour cells, but spares the surrounding healthy tissue.

For purification of the inventive compound, the compound can be coupled to a histidine tag or biotin. In order to verify the binding of the compound of the invention to TA-MUC1, a streptavidin tag or a luminescent or fluorescent dye can be used. The compound can also be coupled to enzymes such as alkaline phosphatase in order to detect tumour cells in the tissue to be analysed. In order to increase the specificity of binding of the compounds of the invention, nano particles can be used for tumour targeting.

In a preferred embodiment, the compounds of the invention can be coupled to CD3 or derivatives of CD3 mAb, for example in the form of CD3-scFv, in order to couple CD3+ T-cells with TA-MUC1-expressing tumour cells. Coupling CD3 to an inventive compound can significantly improve tumour cell lysis by, for example, cytotoxic T-cells.

Preferably, the compound of the invention has a molecular weight between 15 and 100 kDa, more preferably between 25 and 50 kDa. Smaller compounds are preferred as they don't hinder binding to TA-MUC1 due to less steric interference.

Preferably, the compound of the invention is an antibody or antibody fragment such as scFv, wherein the first polypeptide sequence is part of the variable region of the heavy chain ($V_H$) of an antibody and the second polypeptide sequence is part of the variable region of the light chain ($V_L$) of an antibody or antibody fragment.

In a preferred protein compound of the invention, the first polypeptide sequence comprises an amino acid sequence as set forth in SEQ ID NO: 7, and the second polypeptide sequence comprises an amino acid sequence as set forth in SEQ ID NO: 8, or a variant of any one of said amino acid sequences of SEQ ID NO: 7 or SEQ ID NO: 8 having a different amino acid at one or more positions, wherein said variant is capable of binding to mammalian TA-MUC1, preferably hu-TA-MUC1.

Preferably, the first and second polypeptide sequences are part of a polypeptide comprising an amino acid sequence as set forth in SEQ ID NO: 9 or a variant of said amino acid sequence of SEQ ID NO: 9 having a different amino acid at one or more positions, wherein said variant is capable of binding to tumour-associated MUC1.

As shown in the following examples, proteins that are composed of the first polypeptide sequence comprising the amino acid sequences of SEQ ID NO: 1 to SEQ ID NO: 3 and the second polypeptide sequence, comprising the amino acid sequences of SEQ ID NO: 4 to SEQ ID NO: 6 are suitable for recognizing surface-bound TA-MUC1 in tumour tissue, but not in healthy tissue expressing MUC1. As such, the inventive compounds are suitable to differentiate between cancer tissue and normal tissue expressing differentially glycosylated MUC1-subtypes. The following examples also illustrate that the tumour size can be reduced by a preventive immunization against hu-TA-MUC1 by an anti-tumour vaccine applied to induce the inventive compounds. As such, the inventive compounds are suitable for the prevention or treatment of cancer that is characterized by expressing aberrantly glycosylated TA-MUC1.

The invention therefore also relates to a pharmaceutical composition, comprising a compound as described above, and optionally a pharmaceutically suitable carrier, vehicle, solvent or agent. The invention also relates to an inventive compound for use in the prevention, treatment or detection of cancer that is characterized by TA-MUC1-expressing tumour cells. Preferably, the cancer to be treated or prevented by an inventive compound is selected from the group consisting of pancreatic cancer, prostate cancer, breast cancer, B cell leukemia, multiple myeloma, colon cancer and ovarian cancer. As exemplified herein, protein constructs comprising the binding sites of the first and second polypeptide chain are able to bind to mammalian TA-MUC1, preferably hu-TA-MUC1, and are suitable for the diagnosis and treatment of MUC1-expressing epithelial cancers.

The presence of the binding sites within a compound is sufficient for recognizing and binding of the compound mammalian TA-MUC1. Therefore, the invention comprises any compound containing the amino acid sequences of SEQ ID NO: 1 to SEQ ID NO: 6, or homologues thereof from other species that are able to bind to mammalian TA-MUC1, preferably hu-TA-MUC1.

The invention is further illustrated in the following examples.

Constructs

The beneficial therapeutic and diagnostic effects of a compound of the invention were tested with a protein construct bearing the binding sites for hu-TA-MUC1 (=α-hu-TA-MUC1), and which has the following composition:

The first polypeptide sequence of the tested compound comprises the amino acid sequence (SEQ ID NO: 7)
EVKLEESGGGLVQPGGSMKLSCVAS<u>GFTFSDYW</u>MNWVRQSPEKGLEWVA D<u>IRLKSNNYAA</u>HYAESVKGRFTVSRDDSKSSVYLQMNNLRTEDTGFYYC <u>TFGNSFAY</u>WGQGTLVTVSA.

The binding sites of the first polypeptide sequence corresponding to the amino acids SEQ ID NO: 1 (GFTFSDYW), SEQ ID NO: 2 (IRLKSNNYAA) and SEQ ID NO: 3 (TFGNSFAY) are underlined.

The second polypeptide sequence of the tested compound comprises an amino acid sequence (SEQ ID NO: 8)
QAVVTQESALTTSPGETVTLTCRSS<u>TGAVTTNNY</u>ANWVQEKPDHLFTGL IGG<u>TNN</u>RGPGVPARFSGSLIGDKAALTITGAQTEDEAIYFC<u>ALWYSNHW</u>

VFGGGTKLTVL.

The binding sites of the second polypeptide sequence corresponding to the amino acids SEQ ID NO: 4 (TGAVTTNNY), SEQ ID NO: 5 (GTN) and SEQ ID NO: 6 (ALWYSNHWV) are underlined.

The resulting compound is a scFv that comprises the following amino acid sequence containing the binding sites of SEQ ID NO: 1 to SEQ ID NO. 6 (underlined):

(SEQ ID NO: 9)
EVKLEESGGGLVQPGGSMKLSCVAS<u>GFTFSDYW</u>MNWVRQSPEKGLEWVA

D<u>IRLKSNNYAA</u>HYAESVKGRFTVSRDDSKSSVYLQMNNLRTEDTGFYYC

<u>TFGNSFAY</u>WGQGTLVTVSAGGGGSGGGGSGGGGSGGGGSQAVVTQESAL

TTSPGETVTLTCRSS<u>TGAVTTNNY</u>ANWVQEKPDHLFTGLIGG<u>TNN</u>RGPG

VPARFSGSLIGDKAALTITGAQTEDEAIYFC<u>ALWYSNHW</u><u>V</u>FGGGTKLTV

L.

The last leucine (L) in the amino acid sequence of SEQ ID NO: 9 can be followed by a histidine tag (HHHHHH) and/or a streptavidin II tag (WSHPQFEK) for purification and as a marker.

The binding sites within the first and second polypeptide sequences are connected by linker amino acids. The amino acid sequences used to generate α-hu-TA-MUC1 are derived from murine sequences.

Results

Figure 1:
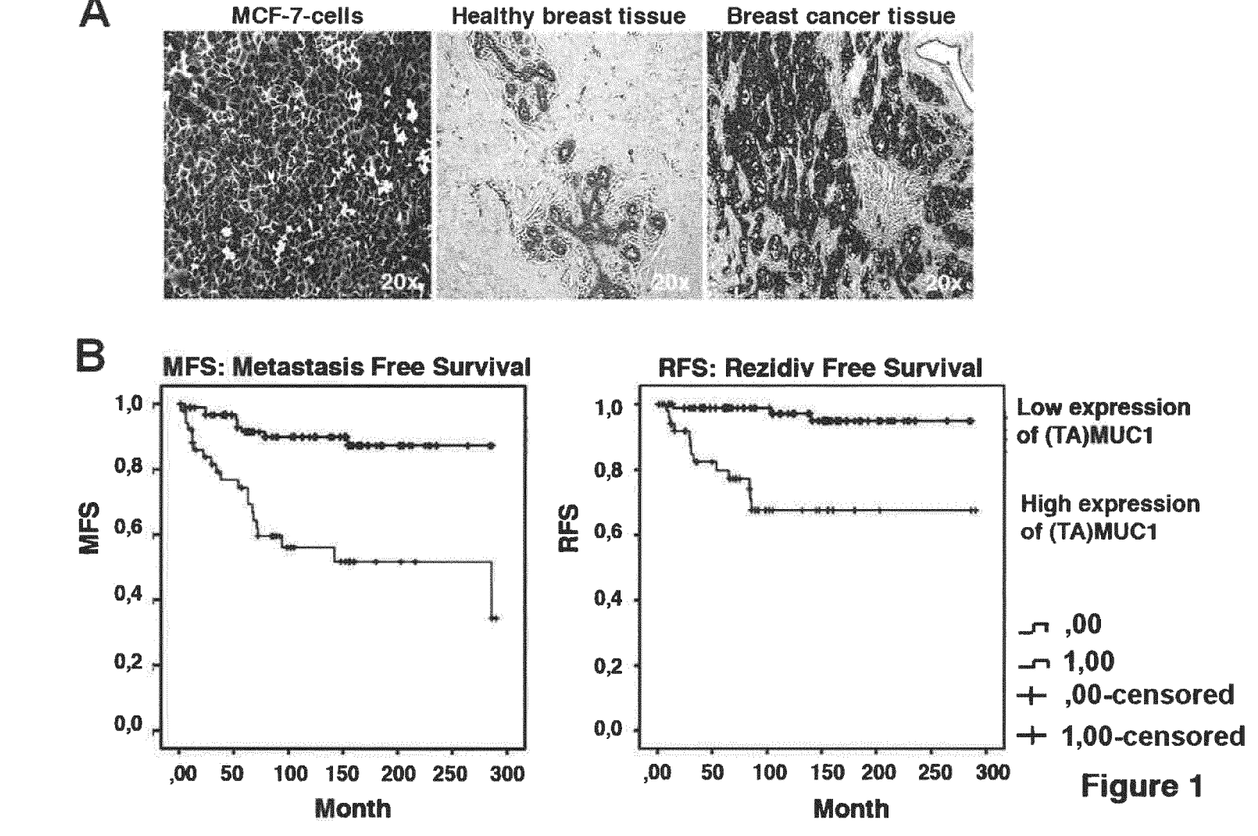
FIG. 1: Histological staining of human breast cancer biopsies against TA-MUC1 with α-hu-TA-MUC1.

FIG. 1 shows a histological staining of human breast cancer biopsies against TA-MUC1 with the mAb underlying the above construct (α-hu-TA-MUC1). 142 sections of human HR+ breast cancer tissue and 10 sections of human breast epithelial tissue were stained with α-hu-TA-MUC1. The treatment of healthy tissue with α-hu-TA-MUC1 showed no colour in all cases. By contrast, all breast cancer tissue sections could be clearly stained with α-hu-TA-MUC1. Exact analysis of staining of breast cancer tissue sections revealed that according to the intensity of staining, two collectives could be distinguished. Accordingly, a correlation was established between the strength of TA-MUC1 expression (staining intensity) and the survival rate of metastasis-free (MFS) and relapse-free patients (RFS). Analysis of the patients' cumulative survival clearly correlated with the level of TA-MUC1 expression. High expression of the tumour marker resulted in a significantly worse survival rate. The immune histological analyses confirm the high specificity of the used TA-MUC1-glycopeptides as antigens for the synthetic breast cancer vaccines. To evaluate the therapeutic effect of these vaccines in vivo, a preclinical breast cancer mouse model was established.

Figure 2:
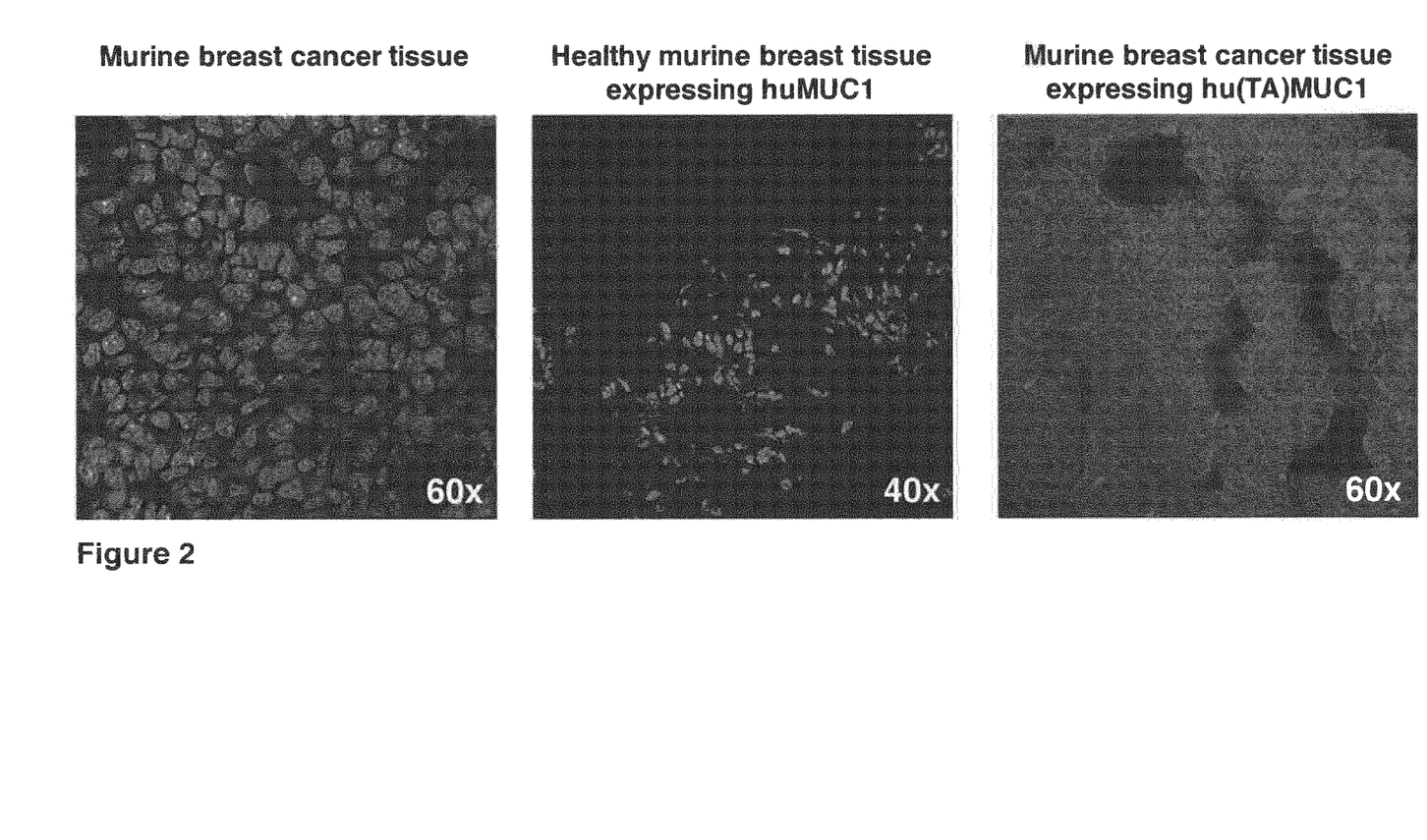
FIG. 2: Immunohistochemistry staining of cryogenic tissue sections of mammary glands and mammary gland tumours against hu-TA-MUC1 with α-hu-TA-MUC1.

PyMT-transgenic (PyMT-tg) mice represent a highly suitable preclinical tumour model to develop therapeutic strategies for the treatment of human breast cancer. The morphological similarities and the expression of biomarkers associated with poor outcome (overexpression of Her2/neu and loss of estrogen and progesterone receptors) are consistent with those in humans. By crossing huMUC1-tg mice (C57BU6-TG(MUC1)79.24GEND/J), expressing huMUC1 on every epithelial cell, with PyMT-tg mice which develop aggressive palpable mammary gland tumours (breast tumours) fourteen weeks after birth, the inventors were able to develop a preclinical breast cancer model that, like 90% of all human epithelial breast cancers, express hu-TA-MUC1. This model offers the possibility to establish an active immune therapy that targets hu-TA-MUC1 to treat breast cancer with the opportunity to apply the same or a similar strategy in a clinical setting. A major obstacle concerning the use of altered self-antigens such as TA-MUC1 as a target for vaccinations are autoimmune responses. Logically, unspecific binding to healthy tissue by induced serum antibodies needs to be excluded. Therefore, binding of the mAb, α-hu-TA-MUC1, initially generated with the aid of the same vaccine used for the following preventive vaccination studies, was checked using healthy mammary gland tissue of tumour-free huMUC1-tg mice via fluorescence microscopy. Binding to healthy mammary gland epithelial tissue, i.e. to fully glycosylated huMUC1, as well as to breast tumour cells from PyMT-tg mice that do not express huMUC1 was not detectable. However, a strong binding of α-hu-TA-MUC1 to breast tumour tissue of PyMTxhuMUC1-tg mice was observed, indicating that a tumour-specific variant of huMUC1 was expressed from breast tumour cells of such mice (see FIG. 2).

After proving the expression of the hu-TA-MUC1 in breast tumour cells of PyMTxhuMUC1-tg mice, a primary tumour cell line was established to develop a transplantable breast tumour model for preventive vaccination studies. As negative control, a primary tumour cell line from PyMT tumour-bearing mice which did not express hu-TA-MUC1 was established in parallel. The huMUC1 expression of primary tumour cells derived from PyMTxhuMUC1 and from PyMT primary tumour cell lines were comparatively analysed via qRT-PCR, and the surface expression of the hu-TA-MUC1-glycoprotein was determined by FACS analyses employing α-hu-TA-MUC1.

Figure 3:
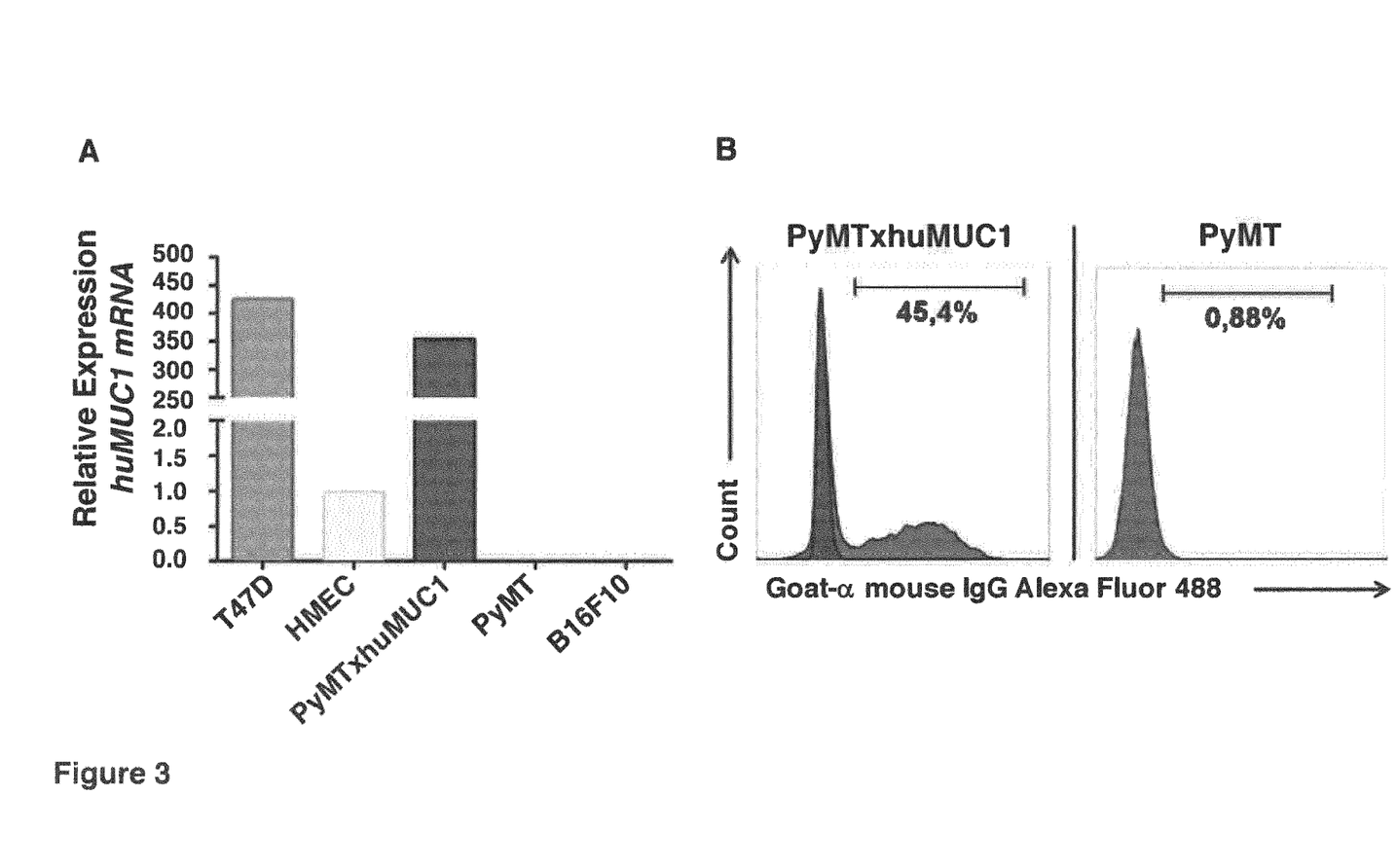
FIG. 3: PyMTxhuMUC1 murine tumour cells from primary tumour cell lines express human MUC1.

FIG. 3A shows the expression of huMUC1 mRNA in PyMTxhuMUC1 cells compared to the expression in human breast cancer cells (T47D) and in human mammary epithelial cells (HMEC), the latter express fully glycosylated MUC. The strongest expression of huMUC1 mRNA was found in T47D cells closely followed by PyMTxhuMUC1 cells. The healthy breast epithelial cell line HMEC expressed much less huMUC1 mRNA underlining that cancer cells overexpress huMUC1. Tumour cells derived from PyMT-tg mice (PyMT cells) do not express huMUC1 mRNA, similar to the murine B16F10 melanoma cells which were chosen as negative control. α-hu-TA-MUC1 mAb bound to a considerable quantity of PyMTxhuMUC1 breast tumour cells while it failed to recognize PyMT breast tumour cells indicating an exclusive expression of hu-TA-MUC1-glycoprotein on PyMTxhuMUC1 cells (see FIG. 3B).

In the next approach with the aid of a well-controlled preclinical autochthonous breast cancer model, the inventors wanted to investigate in a first attempt whether preventive vaccination leads to a mobilisation of the immune system strong enough to reject emerging breast tumours which express hu-TA-MUC1. In this sense, PyMTxhuMUC1 mice and PyMT-tg mice were immunised with the synthetic vaccine three times at intervals of two weeks. Five days after the last immunisation, blood samples were taken and antibody titres and isotypes were determined. Tumour progression was monitored every third day. Because of the oval shape, the size of the tumours was measured by length× width ($mm^2$).

Figure 4:
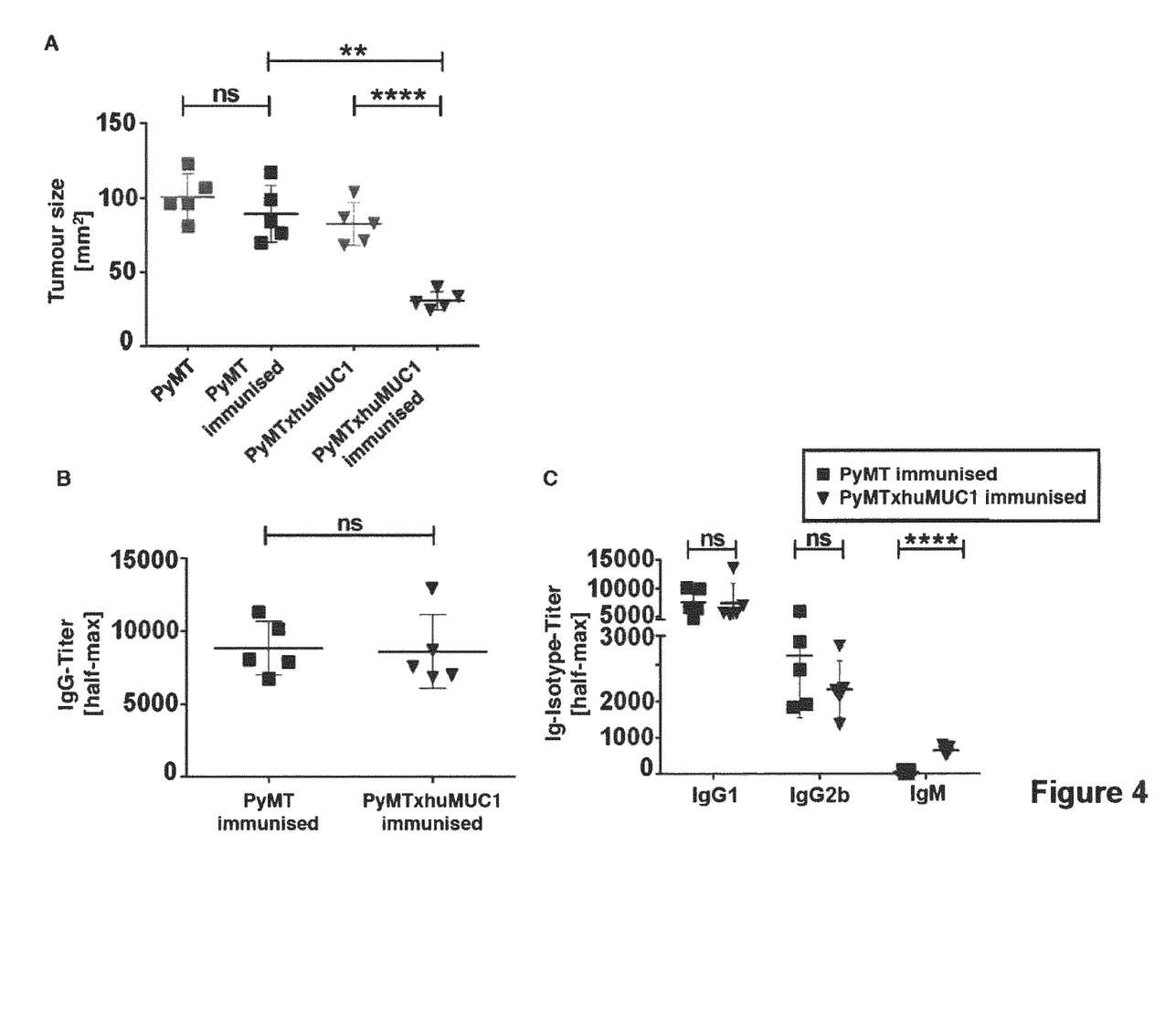
FIG. 4: Reduction of the tumour size through preventive immunisation against hu-TA-MUC1.

FIG. 4A demonstrates that immunised PyMTxhuMUC1-tg mice developed significantly smaller tumours than non-immunised PyMTxhuMUC1-tg mice. On the contrary, immunised PyMT-tg mice showed no tumour reduction in comparison to untreated PyMT-tg mice. Although all vaccinated mice revealed similar hu-TA-MUC1-glycopeptide-specific antibody titres after the third vaccination (see FIG. 4B), the induced humoral immune response showed significant tumour-reducing efficiency only in PyMTxhuMUC1-tg mice. Analyses of the isotype antibodies (see FIG. 4C) confirmed that moderate IgG2b titres were generated. Immunised PyMTxhuMUC1-tg mice compared to immunised PyMT-tg mice showed slightly elevated IgM titres, possibly as a result of a residual T cell tolerance in the PyMTxhuMUC1 double-tg mice. Nevertheless, an overall strong humoral immune response in the absence of autoimmune reactions was observed, confirming the results of previous vaccination studies in huMUC1-tg mice.

In an additional experiment, the inventors investigated the correlation between tumour reduction through preventive vaccination and the survival time. To this end, PyMTxhuMUC1-tg mice were immunised 3 times starting at an age of six weeks after birth. Five days after the last immunisation blood samples were taken to determine the IgG titres and the antibody isotypes. Untreated PyMTxhuMUC1-tg mice served as control. Mice were sacrificed when the survival of the animals was severely restricted according to ethical guidelines.

Figure 5:
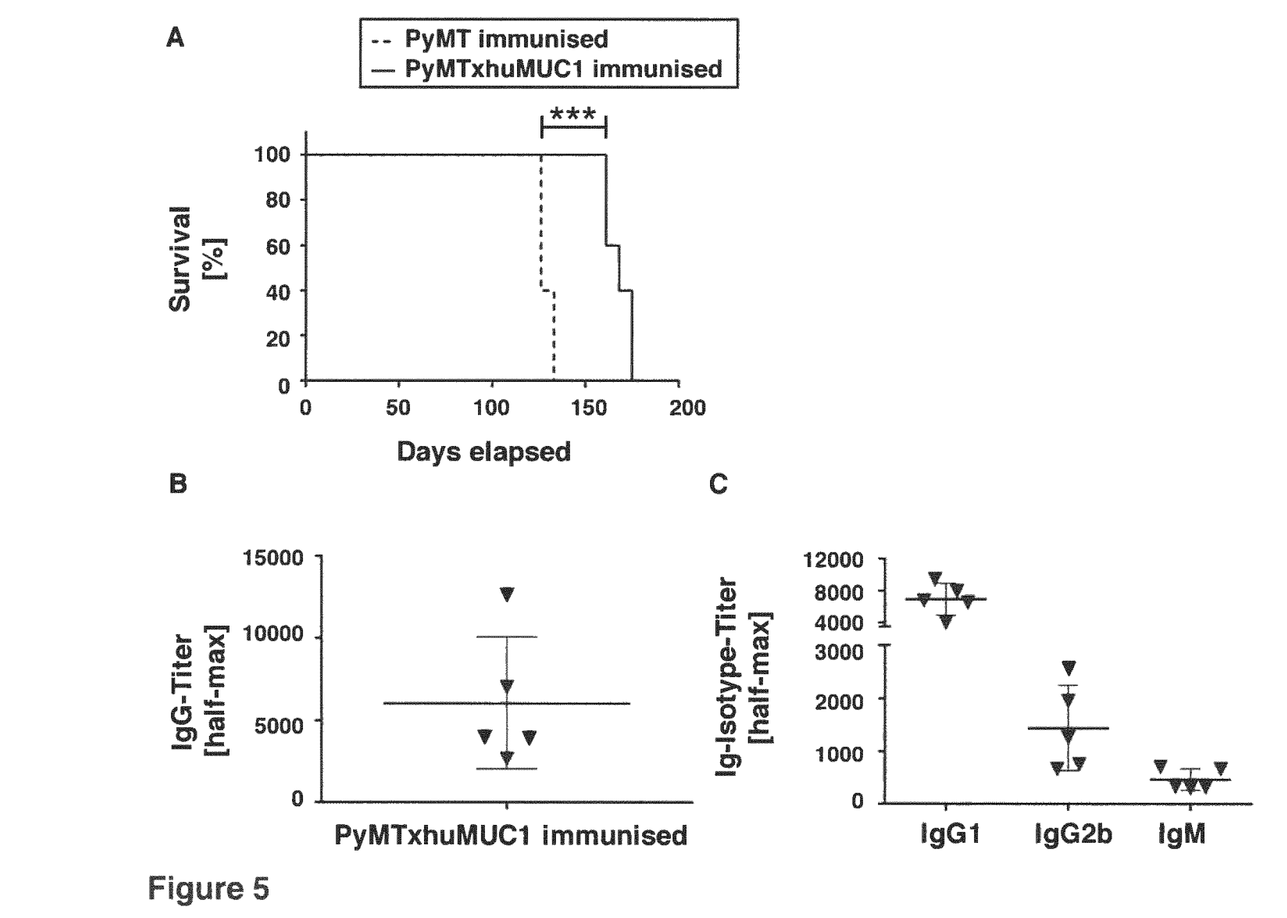
FIG. 5: Prolongation of survival of breast tumour bearing mice through preventive immunisation against hu-TA-MUC1.

FIG. 5A shows that preventively vaccinated, breast cancer bearing mice lived approximately thirteen days longer than untreated mice. ELISA analyses of total IgG titres (see FIG. 5B) and isotype titres (see FIG. 5C) demonstrated the induction of a strong and specific humoral immune response against hu-TA-MUC1 in agreement with the results of the previous experiment (see FIG. 4). Sera from non-immunised tumour-bearing mice did not exhibit any hu-TA-MUC1-glycopeptide antibody titre nor binding to MUC1-expressing T47D human breast cancer cell line or PyMTxhuMUC1 primary tumour cell line (data not shown).

The presence of the binding sites within a compound is sufficient for recognizing and binding of the compound to mammalian TA-MUC1. Similar results were obtained with other compounds bearing the amino acid sequences of SEQ ID NO: 1 to SEQ ID NO: 6, or homologues thereof from other species that are able to bind to mammalian, preferably human TA-MUC1.

Conclusion

The data show that the α-hu-TA-MUC1 is a biologically and pharmaceutically effective compound which is suitable to specifically detect tumour tissue by binding to hu-TA-MUC1 as found on tumour cells but not on normal epithelial cells. Compounds bearing the inventive six binding sites allow the selective detection of tumour tissue within tissue samples. The data also illustrate that α-hu-TA-MUC1 is suitable for the treatment of epithelial tumours as illustrated by breast tumours. A preventive immunisation prolongs the survival of patients suffering from breast tumours. Thus, the inventive protein compounds are suitable for the treatment, prevention and/or diagnosis of cancers that express TA-MUC1 such as breast cancer, pancreatic cancer, prostate cancer, B cell leukemia, multiple myeloma, colon cancer or ovarian cancer. Therefore, any tumour cell that expresses TA-MUC1 is a valid target for the inventive compounds bearing the six identified binding sites as defined in SEQ ID NO: 1 to SEQ ID NO: 6. The data of the inventors illustrate that in breast cancer patients, high TA-MUC1 levels are negatively correlated with an improved overall survival (MFS, RFS). Therefore the data are clearly indicative that an immunisation strategy based on the vaccine inducing the inventive compound has the potency to inhibit breast tumour progression and metastases.

FIGURE LEGENDS

A: A collective of breast cancer tissue sections from 142 patients was examined for TA-MUC1 specific staining for the diagnosis of breast cancer. Human breast cancer cells (MCF-7) strongly expressing the TA-MUC1 served as a positive control, paraffin sections of healthy glandular tissue and paraffin sections of HR+ breast tumours were examined. A representative example of 142 breast cancer tissue sections and ten mammary tissue sections is shown.

B: Correlation of TA-MUC1 expression with the survival rates of metastasis-free (MFS) and recurrence-free (RFS) patients. Staining intensity (0=negative, 1=weak, 2=medium, 3=strong) multiplied by % fraction of MUC1-positive tumour cells (0=0%, 1=1-10%, 2=11-50%, 3=51-80%, 4=81-100%).

Mammary gland tumour isolated from PyMT-tg mice that do not express hu-TA-MUC1, mammary gland tissue isolated from tumour-free MUC1-tg mice that express huMUC1 and mammary gland tumour isolated from PyMTxhuMUC1 mice that express hu-TA-MUC1 were stained with α-hu-TA-MUC1 labelled with AF647N far-red-fluorescent dye (5 μg/ml).

PyMTxhuMUC1 and PyMT tumours were isolated ex vivo, digested, and single cell tumour cell cultures were obtained.

A: The human MUC1 expression of the generated murine breast tumour cells was determined via qRT-PCR in comparison to human MUC1 expressing cell lines (T47D, positive control). B16F10 melanoma cells served as negative control.

B: FACS analyses using α-hu-TA-MUC1 mAb confirmed the hu-TA-MUC1 protein expression of primary PyMTxhuMUC1-derived breast tumour cell lines.

PyMT-tg mice (n=5) and PyMTxhuMUC1-tg mice (n=5) were immunised three times with 10 μg of hu-TA-MUC1-glycopeptide-TTox vaccine every fourteen days. Untreated PyMT-tg mice (n=5) and untreated PyMTxhuMUC1-tg mice (n=5) served as controls.

A: Twenty weeks old mice were sacrificed, and tumour sizes were determined. The average size in $mm^2$ of every tumour of one mouse was calculated. Two-tailed unpaired t-test. ≤P 0.01, **≤P 0.0001.

B: Half-max titres of IgG antibodies were determined via ELISA after the third immunisation.

C: Half-max titres of different Ig-subtypes were determined via ELISA after the third immunisation. Microtiter plates were coated with the hu-TA-MUC1-glycopeptide-BSA conjugate corresponding to the TA-MUC1-glycopeptide moiety of the vaccine. Only the hu-TA-MUC1 binding antibodies were quantified. Two-tailed unpaired t-test. ****≤P 0.0001.

PyMTxhuMUC1 mice (n=5) were immunised three times with 10 μg of hu-TA-MUC1-glycopeptide-TTox vaccine at intervals of fourteen days. Untreated PyMTxhuMUC1 mice (n=5) served as control mice.

A: Health conditions and behaviour of breast tumour bearing mice were observed. When the tumour size reached approximately 200 $mm^2$ and/or the feeding and the physiological agility was negatively influenced, the mice were sacrificed. The days of survival since birth are displayed. Log-rank Mantel-Cox test, ***≤P 0.001.

B: Half-max titres of IgG antibodies were determined through ELISA after the third immunisation.

C: Half-max titres of different IgG-subtype antibodies were determined via ELISA after the third immunisation. Microtiter plates were coated with the hu-TA-MUC1-glycopeptide-BSA conjugate. Only the hu-TA-MUC1 binding antibodies were quantified.

MATERIAL AND METHODS

Histological Staining of Human Breast Cancer Biopsies

A panel of 142 hormone receptor positive (HR+) breast cancer tissues of patients treated with Tamoxifen in adjuvant therapy was examined for the expression of TA-MUC1 by using α-hu-TA-MUC1 as a diagnostic tool. The samples were stained with α-hu-TA-MUC1 (1 μg/ml), further stained with a biotinylated goat anti-mouse antibody as a secondary antibody and the colour reaction with SA-HPO was added. Human breast cancer cells (MCF-7) expressing the TA-MUC1 strongly served as a positive control, paraffin sections of healthy glandular tissue and paraffin sections of HR+ breast cancer tumours were examined. Additionally, the magnitude of expression of TA-MUC1 was scored in correlation of cumulative survival to metastasis (MFS) and relapse-free (RFS) survival according to the scoring system of Sinnet P R et al. (Sinnet P R et al., Comparative Study on The Diagnostic Accuracy of The Ripasa Score Over Alvarado Score In The Diagnosis of Acute Appendicitis Jebmh. 2016; 3(80):4318-21).

Preclinical Breast Cancer Mouse Model Expressing Human MUC1

C57BL/6-TG(MUC1)79.24GEND/J mice (short: huMUC1-tg, The Jackson laboratory) express the human MUC1 gene on all epithelial cells and are crossed with mice of the breast cancer model strain PyMT. Female mice (PyMTxhuMUC1-tg) which are positive for the breast cancer antigen and the huMUC1 transgene develop several mammary gland tumours (four to five tumours per mouse) expressing hu-TA-MUC1, comparable to human breast cancer stage IV after 14 weeks.

Hu-TA-MUC1-Glycopeptide-TTox Vaccine

A synthetic MUC1-derived glycopeptide vaccine that targets a specific MUC1 glycan pattern on human breast cancer cells was generated to produce α-hu-TA-MUC1. The glycopeptide moiety represents a 22mer amino acid sequence from the VNTR region of huMUC1. It includes two immune dominant motifs, the APDTRP and the STAPPA sequences. The serine at position 17 of the STAPPA motif was glycosylated with a $ST_N$ carbohydrate antigen. The synthetic hu-TA-MUC1-glycopeptide was conjugated to Tetanus toxoid (TTox) carrier protein which is known to induce strong T helper cell-specific immune responses in humans. The synthetic vaccine was dissolved in PBS and emulsified (ratio 1:1) in Incomplete Freund's Adjuvant (IFA, Sigma Aldrich). 10 µg/40 µl emulsion were injected intraperitoneal (i.p.) per mouse per immunization.

Fluorescence Microscopy—Binding of α-hu-TA-MUC1 to Murine Breast Tumour Tissues Ex Vivo To establish the above described PyMTxhuMUC1-tg mice as a preclinical breast cancer model for preventive vaccination studies, tumour tissues of PyMTxhuMUC1-tg mice were first tested concerning their expression of hu-TA-MUC1-glycoproteins. To this end, binding of fluorescence labelled α-hu-TA-MUC1 (AF647N: far-red-fluorescent dye) was tested via fluorescence microscopy. Tumours were removed ex vivo, frozen in liquid nitrogen and tissue sections were prepared. The sections were transferred to slides, stained with DAPI (1/1000) and with AF647N-α-hu-TA-MUC1 (5 µg/ml), washed three times and mounted with coverslips. Mammary gland sections of huMUC1-tg mice and tumour sections of PyMT-tg mice served as controls. Confocal microscope LEICA TCS SP8 with DMi8 microscope and Zeiss LSM510 META laser scanning microscope was used to obtain the fluorescence images.

Generation of Primary Cell Lines Using Ex Vivo Isolated Tumours from PyMTxhuMUC1-Tg and PyMT-Tg Mice With the aim to monitor breast tumour growth in detail after preventive vaccination, the inventors generated primary tumour cell lines derived from tumours of PyMTxhuMUC1-tg mice. To this end, tumour tissues were extracted, digested by collagenase A (Roche, 2 mg/ml) and RQ1 DNAse (Promega, 1:2000) and cultured in IMDM+10% FCS+1% glutamine+1% sodium pyruvat. PyMTxhuMUC1 tumour cells and PyMT cells were harvested after 6 weeks. The expression of huMUC1 was tested by quantitative Real-time PCR (qRT-PCR), and binding of α-hu-TA-MUC1 was tested against hu-TA-MUC1-glycoprotein on both cell lines by FACS analyses (see below).

Determination of the Expression of huMUC1 by PyMTxhuMUC1 Tumour Cells Via qRT-PCR and FACS Analyses qRT-PCR:

RT-Total RNA of $2 \times 10^6$ tumour cells was prepared using TRIzol reagent (Invitrogen®, Life technologies, Carlsbad, CA) according to the manufacturer's instructions. The RNA concentration and quality was measured by photometry (Eppendorf BioPhotometer plus). Reverse transcription was performed using the MMLV reverse transcriptase (Thermo Scientific, Dreieich, Germany) according to the manufacturer's instructions and qRT-PCR data were obtained with the following primers: huMUC1 for: 5'-GTGCCCCCTAGCAGTACCG-3', rev: 5'-GACGTGCCCCTACAAGTTGG-3', and as reference gene: EF-1a for: 5'-TGGATGCTCCAGGCCATAAGGA-3', rev: 5'-TGCTCTCGTGTTTGTCCTCCAG-3' by using the 5 times Hot Start Taq EVA Green (no rocks) mix (Axon, Kaiserslautern, Germany) in the MyIQ iCycler (Biorad, Munich, Germany) and the provided software (Bio-Rad iQ5 Standard Version 2.0) for data analysis. Human breast cancer cell line T47D and human mammary epithelial cell line (HMEC) served as positive control for huMUC1 expression. B16F10 murine melanoma cell line served as negative control for huMUC1 expression.

FACS Analyses:

$2 \times 10^5$ PyMTxhuMUC1 and PyMT tumour cells were each incubated with 1 µg/ml α-hu-TA-MUC1 for 20 minutes at 4° C. The cells were washed two times with 100 µl of PBS and then incubated for 20 minutes at 4° C. with a secondary antibody goat-α-mouse-IgG Alexa Fluor 488 (dilution 1:1000 in PBS) and with a fixable viability dye eFluor780 (dilution 1:1000 in PBS) to exclude false positive dead cells. The cells were washed again two times with 100 µl PBS. The cells were then taken up in 100 µl of PBS and analysed on a BD Biosciences FACS LSR II machine. For each sample $10^4$ cells were analysed.

Vaccination of Transgenic Mice Developing Spontaneous Breast Tumours by Administering the hu-TA-MUC1-Glycopeptide-TTox Vaccine PyMTxhuMUC1-tg and PyMT-tg mice (the latter as control) were immunised three times at intervals of two weeks (i.p. 10 µg/40 µl) starting at age of six weeks. Five days after each vaccination, blood was collected from the tail vein and serum was collected therefrom. The antibody titres and the isotype titres of the induced antibodies were determined by ELISA (data from the first and second immunisation are not shown). Immunised mice and untreated mice were sacrificed after twenty weeks, all tumours were isolated and quantified with a calliper. Because of the oval shape of the tumours and the wavy surface, length×width were calculated ($mm^2$). Every PyMTxhuMUC1-tg and PyMT-tg mouse developed four to five mammary gland tumours. Tumour size is given as average of the number of tumours for each mouse. Survival of immunised PyMTxhuMUC1-tg mice in comparison to untreated PyMTxhuMUC1-tg mice was given in days after birth. The survival of the mice was monitored according to ethical guidelines.

Analyses of hu-TA-MUM-Specific Antibody Titres and Antibody Isotypes Via ELISA

For analysing the IgG titres of hu-TA-MUC1-glycopeptide-specific induced antibodies, ELISA was applied. The 96-well plates (Nunc MaxiSorp® flat-bottom) were incubated with 50 µl per well of hu-TA-MUC1-glycopeptide-BSA conjugate (2.5 µg/ml) in coating buffer (0.1 M $Na_2HPO_4$ in water, pH 9.3) at 37° C. Washing steps (three times) were processed using 100 µl blocking buffer (1% BSA, 0.2% Tween-20 in PBS). In order to saturate free binding sites, the coated plates were subsequently incubated for 20 minutes with 50 µl blocking buffer at 37° C. Antisera were diluted in blocking buffer (1:100 for the first column of the 96-well plate and then serially diluted in a ratio of 1:1), pipetted on the ELISA-plate and incubated for 45 minutes at 37° C. After three additional washing steps, the samples were incubated with biotinylated sheep-α-mouse IgG antibody (c=0.48 µg/ml, stock solution 250 µg/ml) for 45 minutes at 37° C. in 50 µl blocking buffer per well. The plates were washed three times and incubated for 15 minutes with streptavidin-horseradish peroxidase (1:1000) in 50 µl blocking buffer. After washing three times, each well was treated with 1 mg/ml 2,2'-azino-bis(3-ethylbenzothiazoline-6-sulphonic acid) (ABTS), 0.01% hydrogen peroxide (1:4000) in citrate buffer (40 mM citric acid, 60 nM $Na_2HPO_4 \times H_2O$, pH 4.5). The optical density of each well was measured at 410 nm with a spectrophotometer (Tecan Reader, Genios).

For isotype determination hu-TA-MUC1-glycopeptide-specific antisera were analysed after the third immunisation, ELISA was carried out using the protocol described above. The following secondary antibodies were used: biotinylated anti-mouse-IgM (eBioscience, clone eB121-15F9), biotinylated anti-mouse-IgG1 (BD Pharmingen, clone A85-1), biotinylated anti-mouse-IgG2b (BD Pharmingen, clone R19-15).

The antibody titres were calculated as half-max by a non-linear regression ($R^2 > 0.97$) followed by a four-parameter logistic curve analysis applying the software GraphPad Prism 6.

The invention claimed is:

1. Peptide based compounds comprising:
   a first polypeptide sequence comprising at least three different amino acid sequences selected from the group consisting of GFTFSDYW (SEQ ID NO: 1), IRLKSN-NYAA (SEQ ID NO: 2), and TFGNSFAY (SEQ ID NO: 3), and having an amino acid sequence as set forth in SEQ ID NO: 7, and
   a second polypeptide sequence comprising at least three different amino acid sequences selected from the group consisting of TGAVTTNNY (SEQ ID NO: 4), GTN (SEQ ID NO: 5), and ALWYSNHWV (SEQ ID NO: 6), and having an amino acid sequence as set forth in SEQ ID NO: 8,
   wherein said peptide based compounds are capable of binding to tumour-associated Mucin-1 (TA-MUC1).

2. The peptide based compounds according to claim 1, wherein the first polypeptide sequence and the second polypeptide sequence are covalently coupled by a linker.

3. The peptide based compounds according to claim 2, wherein the linker comprises one or more amino acids selected from the group consisting of S and G.

4. The peptide base compounds according to claim 1, wherein the peptide based compounds are a protein, antibody, scFv or hybrid fusion protein.

5. The peptide based compounds according to claim 1, wherein the peptide based compounds are labelled with $^{89}$Zr or $^{117}$Lu.

6. The peptide based compounds according to claim 1, wherein the peptide based compounds are coupled to biotin, streptavidin, histidine, a luminescent or fluorescent dye, nanoparticles, or alkaline phosphatase.

7. The peptide based compounds according to claim 1, wherein the peptide based compounds are coupled to derivatives of mAb CD3 for attracting CD3+ cytotoxic T cells.

8. The peptide based compounds of claim 1, wherein the first polypeptide sequence is part of the variable region of the heavy chain ($V_H$) of an antibody and the second polypeptide sequence is part of the variable region of the light chain ($V_L$) of an antibody or antibody fragment.

9. The peptide based compounds of claim 1, wherein the first polypeptide sequence and the second polypeptide sequence are part of a polypeptide comprising an amino acid sequence as set forth in SEQ ID NO: 9.

10. A pharmaceutical composition, comprising the peptide based compounds according to claim 1.

11. The pharmaceutical composition according to claim 10, comprising a pharmaceutically suitable carrier, vehicle, solvent or agent.

* * * * *